United States Patent [19]

Kielbania, Jr. et al.

[11] Patent Number: 5,277,979
[45] Date of Patent: Jan. 11, 1994

[54] PROCESS FOR MICROENCAPSULATION

[75] Inventors: Andrew J. Kielbania, Jr., Chalfont; William D. Emmons, Huntingdon Valley; George H. Redlich, Norristown, all of Pa.

[73] Assignee: Rohm and Haas Company, Philadelphia, Pa.

[21] Appl. No.: 882,323

[22] Filed: May 13, 1992

Related U.S. Application Data

[62] Division of Ser. No. 581,439, Sep. 12, 1990, Pat. No. 5,225,278.

[51] Int. Cl.$^5$ .............................................. B01J 13/16
[52] U.S. Cl. ................................ 428/402.21; 264/4.3; 264/4.7; 424/408; 424/462; 424/497; 427/213.33; 427/213.34; 428/402.22; 428/402.24; 514/963
[58] Field of Search .................. 264/4.3, 4.7; 424/408, 424/462, 497; 427/213.33, 213.34; 428/402.21, 402.22, 402.24; 514/963

[56] References Cited

U.S. PATENT DOCUMENTS 3,872,023 3/1975 Baum et al. ...................... 252/316

FOREIGN PATENT DOCUMENTS

1091078 11/1967 United Kingdom .

Primary Examiner—John Kight, III
Assistant Examiner—T. Mosley
Attorney, Agent, or Firm—Wendy A. Taylor

[57] ABSTRACT

A process for encapsulating a wide variety of target materials, including both hydrophilic and hydrophobic materials, employs condensation of two reactive compounds to form shells around core phase particles including target material dispersed in a continuous phase. One of the reactive compounds has at least two active methylene functional groups per molecule, the other being an active methylene-reactive crosslinking agent. Either type of the reactive compounds can be dispersed in the continuous phase, the other being dispersible in the core phase. Applications include controlled release microencapsulation of agriculture chemicals and biocides.

10 Claims, 2 Drawing Sheets

Δ = NOT ENCAPSULATED
O = ENCAPSULATED

PROCESS FOR MICROENCAPSULATION

This is a divisional of application Ser. No. 581,439, filed Sep. 12, 1990, now U.S. Pat. No. 5,225,278.

BACKGROUND OF THE INVENTION

1. Field of the Invention

The present invention relates to a process for preparing microcapsules containing a target material, the microcapsules produced thereby, and compositions containing these microcapsules. More particularly, the present invention relates to a polymerization process for microencapsulation.

2. Brief Description of the Prior Art

A variety of methods for the preparation of microcapsules are known. In general, as an initial step one fluid is dispersed within another, the two fluids being immiscible, or nearly so, and in any case forming separate phases. A common example is the oil-in-water (o/w) dispersion, although water-in-oil (w/o) dispersions are also well known, and the only physical criterion for selecting the fluid pair is mutual in-compatibility at the selected temperature and pressure. Often a surface-active dispersant or protective colloid, such as polyvinyl alcohol in the case of oil-in-water dispersions, is dispersed or dissolved in the continuous phase to stabilize the dispersion. The ultimate object is to form a capsular wall or shell around the dispersed phase droplets or particles, the dispersed phase being formed by or containing a target material which is to be encapsulated. Microencapsulation techniques are reviewed in I. E. Vandergaer, *Microencapsulation* (Plenum Press, London 1974). The methods for forming the wall can be broadly divided into physical and chemical techniques.

The physical technique, complex coacervation, involves precipitation of a polymeric species at the interface between the continuous and discontinuous phase. For example, gelatin, dissolved or dispersed in a continuous aqueous phase at controlled temperature and pH, can be coacervated or precipitated at the interphase between the aqueous phase and a dispersed organic fluid phase, by reaction with an anionically charged colloid, such as gum arabic, vinyl acetate-maleic anhydride copolymer, sodium alginate, polyacrylic acid, or the like. The walls or shells formed at the interface can be subsequently hardened by physical or chemical treatment, such as disclosed in U.S. Pat. No. 2,800,457. Coacervation processes typically require careful control over process conditions such as reactant concentrations, temperature, and pH, and employ substantial proportions of a relatively expensive material, gelatin, in forming the capsule shells. The processes are complex, and give microcapsules which typically have poor water resistance.

Numerous chemical techniques for forming the microcapsule shells have also been proposed. For example, urea and formaldehyde or a urea-formaldehyde precondensate can be dispersed in a continuous aqueous phase, and subsequently induced to react to give a urea-formaldehyde condensate which forms encapsulating shells around a dispersed phase containing the target material. Urea-formaldehyde microencapsulation is taught, for example, in U.S. Pat. Nos. 3,016,309 and 3,796,669. The use of polymeric species such as gum arabic, polyacrylic acid, alkyl acrylate-acrylic acid copolymers, and hydrolyzed poly(ethylene-co-maleic anhydride) to modify the properties of urea-formaldehyde shells is reviewed in U.S. Pat. No. 4,552,811. Processes in which the microcapsule shell polymer is polymerized in either the continuous phase or the discontinuous phase are often referred to as "in-situ" techniques.

The in-situ shell-forming materials can be included in the discontinuous phase. For example, U.S. Pat. No. 4,626,471 discloses in-situ polymerization of certain multifunctional epoxy resins using polyamine curing agents. The epoxy resin and amine are emulsified in aqueous solution, and the temperature is elevated to promote cure of the resin. The cured resin migrates to the interface to form the shells of the microcapsules.

Another set of methods for encapsulating target materials involves interfacial polymerization, the polymeric shell being polymerized at or near the interface between the continuous and discontinuous phases. Typically, the polymerization reaction is a condensation or addition reaction involving two types of difunctional monomer, the first being dissolved or dispersed in the continuous phase, the second being dissolved or dispersed in the discontinuous phase.

For example, U.S. Pat. No. 4,622,267 discloses an improved interfacial polymerization technique for preparing microcapsules for carbonless copy paper. The target material (color-former) is initially dissolved in a good solvent and an aliphatic diisocyanate soluble in the good solvent/color former mixture is added. Subsequently, a poor solvent for the aliphatic diisocyanate is added until the turbidity point is just barely reached. This organic phase is then emulsified in an aqueous solution, and a reactive amine is added to the aqueous phase. The amine diffuses to the interface, where it reacts with the diisocyanate to form polymeric polyurethane shells. A similar technique, used to encapsulate salts which are sparingly soluble in water in polyurethane shells, is disclosed in U.S. Pat. No. 4,547,429.

An interfacial photopolymerization method is disclosed in U.S. Pat. No. 4,532,183. In this addition polymerization technique, free radical polymerizable monomers are present in both a continuous aqueous phase and a discontinuous oil phase. The aqueous phase can include a hydroxyalkyl acrylate or methacrylate while the oil phase can contain copolymerizable ethylenically unsaturated oil soluble monomer such as an alkyl acrylate. Photoinitiator can be added to either phase, and a polyfunctional isocyanate prepolymer is preferably added to the oil phase to enhance shell formation.

Microcapsules have been used to encapsulate a great variety of target materials. The most important commercial use of microencapsulated materials has been in the manufacture of carbonless copy paper. Typically, a colorless dye precursor or color-former such as crystal violet lactone is encapsulated in microcapsules having fairly rigid shells, and a slurry containing the microcapsules is coated onto the back of a first sheet (CB sheet). The face of a second sheet is coated with an acid, color developing material such as an acidic clay or a phenolic resin (CF sheet). The sheets are manufactured into a form with the CB sheet over the CF sheet. Pressure on the CB sheet, such as that generated by the ball of a ball-point pen, ruptures the shells of the microcapsules to free the dye-precursor to react with the color developer and form a copy of the original on the CF sheet.

Other microencapsulated target materials have included agricultural chemicals, food for newly hatched fish, pharmaceuticals, pesticides, flavorings, scents, adhesives, toners for xerography, fertilizers, inks, toxic salts and crosslinking agents and other reactive chemicals. The nature of the application strongly influences the characteristics of the polymeric shells. For example, in the case of encapsulated pharmaceuticals, sustained, gradual release of the target material from the microcapsules may be desired, and the shell porosity and/or biodegradability could be controlled to achieve the desired release kinetics. In the case of carbonless copy paper, the microcapsules must be rigid for easy rupturability, and relatively impervious to diffusion by the color-former for stability.

Microencapsulation techniques are often directed to the problems associated with encapsulating specific target materials and cannot be easily generalized to different types of target materials. For example, the in situ polymerization of urea-formaldehyde precondensates to encapsulate dispersed oil phase droplets containing color former cannot be easily adapted to target materials requiring water-in-oil encapsulation, such as water-soluble vitamins. There is a need for an encapsulation process of sufficient breadth such that a wide variety of target materials can be successfully encapsulated. In particular, there is a need for an encapsulation process which can be used to encapsulate both hydrophilic target materials, such as water-soluble target materials, and hydrophobic target materials, such as oil-soluble target materials.

SUMMARY OF THE INVENTION

The present invention provides a process for microencapsulating a target material in a dispersion of insoluble core-shell particles which are dispersed in a continuous fluid phase. This process is applicable to encapsulating a wide variety of target materials, including both hydrophobic and hydrophilic target materials. The process employs the polymerization reaction of a first reactive compound with a second reactive compound, one of these compounds being a compound having at least two active methylene functional groups per molecule, the other compound being a active methylene-reactive crosslinking agent.

The process comprises preparing a core emulsion including a core phase of discrete core particles dispersed in the continuous fluid phase. The core emulsion is prepared by emulsifying a mixture comprising:

(1) a target material, and (2) a dispersant for the core particles in the continuous phase. Preferably, the mixture also contains a first reactive compound insoluble in the continuous fluid phase, the first reactive compound being selected from one of (1) compounds having at least two active methylene functional groups per molecule, and (2) active methylene-reactive crosslinking agents. However, the first reactive compound can be added to the continuous phase after the core emulsion has been prepared.

The process further includes combining with the continuous fluid phase a second reactive compound soluble or dispersible in the continuous phase and selected from one of (1) compounds having at least two active methylene functional groups per molecule, and (2) active methylene-reactive crosslinking agents, the first reactive compound reacting with the second reactive compound to form polymeric encapsulating shells around the cores.

In one embodiment of the process, the continuous fluid phase includes water; for example, it can be an aqueous solution. In this embodiment the core phase and the target material are hydrophobic, and the first reactive compound is water-insoluble. The first reactive compound can be selected from water-insoluble compounds which have at least two active methylene functional groups per molecule. If so, the second reactive compound can be selected from water-soluble active methylene-reactive crosslinking agents.

The broad applicability and generality of the present process is apparent. Starting with a specific target compound, the choice of the first and second reactive compounds, as well as the character of the continuous and dispersed phases, can be selected to reflect the physical and chemical properties of the target compound. Thus, a great variety of target materials can be microencapsulated using the process of the present invention.

The microcapsules produced by the present process can be separated from the continuous phase if desired. The microcapsules containing the target material can be adapted to either sudden release or sustained release applications, such as carbonless copy paper and agricultural chemical microcapsulation, respectively, by choice of first and second reactive materials to give polymeric shells with appropriate physical properties.

Another advantage of the process of the present invention is that it can be used to produce microcapsules having diameters on order of 0.5 micron and less, significantly less than the diameter of microcapsules produced using many common techniques.

The microencapsulation process of the present invention is applicable to a wide variety of target materials, including both hydrophilic materials, such as water-soluble pesticides, for example, ethylene bis-dithiocarbamate salt fungicides and Kathon ® (trademark of Rohm and Haas Co.) biocide, and hydrophobic materials such as water-insoluble pesticides, for example, Karathane ® (trademark of Rohm and Haas Co.) and Skane ® (trademark of Rohm and Haas Co.) M-8 mildicide. Other types of target materials which can be encapsulated using the present process include color-formers for carbonless copy paper, such as crystal violet lactone, benzoyl leuco methylene blue, the paratoluene sulfonate of Michler's Hydrol, 3-diethylamine-6-methyl-7-anilofluran, and the like. Reactive chemicals such as di and poly- isocyanates, organic peroxides, and epoxy-functional compounds can also be encapsulated. Similarly, pharmaceuticals, scents, flavorings, xerographic toners, inks, catalysts, fertilizers, adhesives, inorganic salts, photosensitizers, photoactivators, reactive chemicals, and a great variety of other target materials can be microencapsulated using the process of the present invention. More than one target material can be microencapsulated simultaneously by the present process, as in the case where two target materials are mutually soluble.

When hydrophobic target materials are to be encapsulated, a hydrophilic continuous fluid phase, such as water or an aqueous or alcoholic solution, is employed. The hydrophobic target material is dispersed in the hydrophilic continuous phase, along with at least one hydrophobic first reactive compound. Conversely, when hydrophilic target materials are to be encapsulated, a hydrophobic continuous phase, such as an oil or nonaqueous organic solvent, is employed. The hydrophilic target material is dispersed in the hydrophobic continuous phase, along with at least one hydrophilic first reactive compound.

The first reactive compound can be initially mixed with the target material, and the mixture subsequently dispersed in the continuous fluid phase, or the first reactive compound can be mixed with the continuous phase after a core phase including the target material has been formed. If desired, a mixture of first reactive compounds can be used.

The use of "first" in "first reactive compound" denotes the compatibility of the compound with the core phase, and is not intended to indicate or suggest an order of addition. Similarly, the use of "second" in "second reactive compound" denotes the compatibility of this compound with the continuous phase, and does not relate to the order of addition.

The first reactive compound can be either a compound having at least two active methylene groups per molecule or a compound being an active methylene-reactive crosslinking agent. The choice of either of these two types of compound for the first reactive compound fixes the character of the second reactive compound, in the sense that the second reactive compound must be selected to be reactive with the first reactive compound. Thus, if the first reactive compound is selected to be a compound having at least two active hydrogen functional groups per molecule, then the second reactive compound must be an active methylene-reactive crosslinking agent. Conversely, should the first reactive compound be selected to be a compound which is an active methylene-reactive crosslinking agent, the second reactive compound must be a compound having at least two active hydrogen functional groups per molecule.

When a hydrophobic target material is to be encapsulated, then the first reactive compound must be sufficiently hydrophobic so that it, along with the hydrophobic target material, form a separate, dispersed, non-continuous phase within the hydrophilic continuous phase. Similarly, when a hydrophilic target compound is to be encapsulated, the first reactive compound must be sufficiently hydrophilic so that it and the target-compound form a dispersed core phase within the hydrophobic continuous phase.

Preferably, the first reactive compound is substantially insoluble in the continuous phase. However, first reactive compounds which are slightly or sparingly soluble in the first continuous phase can also be used in the present process. By "substantially insoluble" is meant having a solubility of less than about one percent by weight. In addition to its being substantially insoluble in the continuous phase, it is preferred that the first reactive compound be miscible with, or soluble in, the target material, such that the core phase includes both the target material and the first reactive compound. The polymeric product of the first and second reactive compounds is preferably insoluble in both the continuous fluid phase and the dispersed core phase.

When a hydrophobic target material is to be encapsulated, it is preferred that the core phase include an "emulsion stabilizer," such as disclosed in U.S. Pat. Nos. 4,336,173 and 4,113,687 (Ugelstad). The emulsion stabilizer is a hydrophobic organic compound which serves to increase the stability of the dispersed core phase, encourages the formation of a fine dispersion of core particles having a narrow particle size distribution, and discourages agglomeration of the individual core particles into particles having dimensions larger than those desired. The choice of the emulsion stabilizer depends to some extent on the target material and the first reactive compound; the emulsion stabilizer is preferably selected to be miscible with both the target material and the first reactive compound. When the target material and the first reactive compound are not completely miscible or soluble in one another, it may be possible to select an emulsion stabilizer in which both the target compound and the first reactive compound are both soluble. Preferably, the emulsion stabilizer, the first reactive compound, and the target material form a ternary solution, dispersed as the core phase in the hydrophilic continuous fluid phase.

Examples of emulsion stabilizers which can be used in the process of the present invention include the dialkyl phthalate esters, such as dibutyl phthalate, dimethyl phthalate, and dioctyl phthalate; alkyl aralkyl phthalates such as butyl benzyl phthalate; solvents for target materials, including alkyl naphthalenes, phenylxylylethanes, alkylbiphenyls, polyhalogenated biphenyls, hydrogenated and partially hydrogenated terphenyls, paraffin oils, chlorinated paraffin oils, mineral oils, trichlorobenzene, nitrobenzene, tricresylphosphate, maleic acid alkyl esters, dibenzylbenzene, linear alkylbenzenes having about 10–14 carbon atoms, polyarylmethanes, petroleum ethers; organic solvents such as toluene, xylene, and the like; and mixtures thereof. The type and quantity of emulsion stabilizer ar selected with the understanding that the emulsion stabilizer will be confined within the microcapsules after polymerization. Thus, emulsion stabilizers which tend to plasticize or dissolve the polymeric microcapsule shells are avoided when rigid, easily rupturable shells are desired. Similarly, emulsion stabilizers which tend to react with the target material or reduce its efficacy are to be avoided.

When the target material is hydrophobic, the first reactive compound can be a hydrophobic compound having at least two active methylene groups per molecule. Similarly, when the target compound is hydrophilic, the first reactive compound can be a hydrophilic compound having at least two methylene groups per molecule.

By "active methylene" group is meant a methylene group having an active, or acidic, hydrogen atom, by virtue of the electron-withdrawing nature of functional groups proximate the active methylene group. Examples of functional groups which contain active methylene groups include functional groups having the structural formula $$-X-C(O)-CH_2-Z,$$

the group X adjacent the carbonyl carbon being selected from $-NR-$, $-O-$, $-S-$, $-O(CH_2CH_2O)_m[CH(CH_3)CH_2O]_n-$, and $-N(CH_2CH_2O)_m[CH(CH_3)CH_2O]_n-$, where m, n=0–4, independently; and the group Z adjacent the methylene group being selected from $-C(O)R$, $-CO_2H$, $-CO_2R$, $-C(O)NHR$, $-C(O)NR_2$, $-CN$, $-NO_2$, $-SOR$, $-SO_2R$, $-SO_3R$, phenyl, and $(C_1-C_3)$alkyl-substituted phenyl; R being selected from $(C_1-C_6)$ alkyl. Thus, such active methylene-containing functional groups as $-O-C(O)-CH_2-CO_2H$, $-N(CH_3)-C(O)-CH-$ 2—$CO_2CH_3$, —S—C(O)—$CH_2SO_3C_2H_5$ and —O—C(O)—$CH_2$—C(O)N$(CH_3)_2$ are included.

Examples of preferred active methylene functional groups include —NHC(O)$CH_2$C(O)$CH_3$, —OC(O)$CH_2$C(O)$CH_3$ (i.e. acetoacetyl), —NHC(O)$CH_2$CN, and —O—C(O)$CH_2$CN (i.e. cyanoacetyl).

In general, the active methylene-containing compound can be prepared by the condensation of a diol or polyol or diamine or polyamine with a compound having the structural formula

H—X—C(O)—$CH_2$—Z where X and Z are given above. Examples of diols and polyols which can be used include diols, such as ethylene glycol, di-ethylene glycol, triethylene glycol, tetraethylene glycol; 1,2-propanediol, 1,3-propanediol, dipropylene glycol, 2,2-di-methyl-1,3-propanediol, 2,2,4-trimethyl-1,3,-pentanediol; di(hydroxyethyl)- and di(hydroxypropyl)- adipate, azelate, dodecanoate, maleate and fumarate; 1,3-butanediol, 1,4-butanediol, 2-buten-1,4-diol, 1,5-pentanediol, 1,6-hexanediol; 1,2-cyclohexanedimethanol, 1,3-cyclohexanedimethanol, 1,4-cyclohexanedimethanol; 1,2-cyclohexanediol, 1,3-cyclohexanediol, 1,4-cyclohexanediol; 1,7-heptanediol, 1,8-octanediol, 2-ethyl-1,3-hexanediol, 1,9-nonanediol, 1,10-decanediol, 1,12-dodecanediol, 4,4'-isopropylidenediphenol and its ethoxylates or propoxylates; 2,2'-thiodiethanol, 3,3'-thiodipropanol; N-methyldiethanolamine, N-ethyldiethanolamine, N-butyldiethanolamine, N-phenyldiethanolamine; and N-methylol-, N-(2-hydroxyethyl)-, and N-(2-hydroxypropyl)-derivatives of bisamides, ureas, and hydantoins, and triols such as glycerol; 2-ethyl-2-(hydroxymethyl)-1,3-propanediol, 1,1,1,-tris(hydroxymethyl)-ethane, or their ethoxylates and propoxylates; triethanolamine; N-methylol-, N-(2-hydroxyethyl) , or N-(2-hydroxypropyl)- derivatives of quanamines, melamine, and cyanuric acid; tetrols such as pentaerythritol; N-methylol-, N-(2-hydroxyethyl)-, or N-2(hydroxypropyl)- derivatives of guanamines, melamine, etc.; hexols such as dipentaerythritol, sorbitol; N-methylol-, N-(2-hydroxyethyl)- or N-(2-hydroxypropyl)- derivatives of melamine; and octols such as tripentaerythritol.

Examples of hydroxy-functional compounds which can be used include low molecular weight hydroxy-functional polymers and oligomers, such as oligomers of hydroxyethyl acrylate and/or hydroxyethyl methacrylate and other hydroxyalkyl acrylates and methacrylates; polyvinylalcohols; and oligosaccharides. Such polymeric or oligomeric hydroxy-functional compounds would tend to form multi-functional active methylene compounds such as multi-functional aceto or cyano-acetates.

When the first reactive compound is to be a hydrophobic active methylene containing compound, the diol or polyol and the group X and R are selected to confer appropriate hydrophobicity. Examples of hydrophobic compounds having at least two active methylene groups per molecule and which can be used as hydrophobic first reactive compounds in the present process include the tris(acetoacetyl)trimethylolpropane, tris(cyanoacetyl)trimethylolpropane, tris(nitroacetyl)trimethylolpropane, bis(N-methyl-N-hydroxyethylcyanoacetamido)adipate, bis(cyanoacetamido)ethoxyadipate, tris(isopropylinolocyanoacetyl)trimethylolpropane, tetra(acetoacetyl)pentaerythritol, tetra(acetoacetyl)erythritol, tris(cyanoacetyl)glycerol, tris(acetoacetamido)melamine, bis(isopropylidiocyanoacetyl)1,4-butylene glycol, bis(cyanoaceto)neopentyl glycol, and bis(acetoacetyl)diethylene glycol.

Mixtures of di- and/or poly-functional alcohols can be condensed with a single active methylene compound, or mixtures of active methylene compound can be condensed with a single di- and/or poly-functional alcohol, or mixtures of di-and/or poly-functional alcohols and mixtures of active methylene compounds can be condensed, in order to prepare compounds having at least two active methylene groups per molecule for use in the process of the present invention, and mixtures of such compounds can be used in the present process.

When the dispersed core phase is hydrophobic, the continuous fluid phase is hydrophilic. Examples of hydrophilic continuous fluid phases which can be used in the process of the present invention include water, alcohols, and aqueous solutions, including alcoholic solutions and aqueous solutions of inorganic salts, e.g. $MgNO_3$, zinc acetate. For example, a saline solution containing from about 0 to 0.25 g NaCl per g of water can be used. Examples of alcohols which can be used include methanol, ethanol, n-propanol, isopropanol, ethylene glycol, diethylene glycol, glycerol, and mixtures thereof.

A hydrophilic continuous fluid phase can include dispersing agents for the dispersed core phase. Examples of dispersing agents include polymeric dispersants and protective colloids such as polyvinyl alcohol, polyvinyl acetate, gum arabic, carboxymethyl cellulose, hydroxyethylcellulose, partially hydrolyzed polyvinyl alcohol, and styrene-maleic anhydride copolymers. The dispersing agents aid in dispersing, setting the particle size and stabilizing the hydrophobic core particles in the hydrophilic continuous phase, as well as maintaining the colloidal stability of the final dispersion, and their use is well known in the art.

Conventional surface active agents, such as are known in the emulsification arts, can also be used to aid in dispersing and stabilizing the hydrophic core phase particles within the hydrophilic continuous phase. Examples of surface active agents which can be used to disperse and stabilize the hydrophobic core phase particles include dialkyl sulfosuccinates, such as diethylhexyl sulfosuccinate and other surface active agents such as sodium lauryl sulfate, sodium dodecylbenzene sulfonate; alkali metal salts of alkylarylpolyethoxyethanol sulfates, sulfonates, or phosphates; stearyldimethylbenzylammonium chloride, etc.

The dispersion of the core phase in the continuous phase can be accomplished by any technique known in the art. For example, a solution including the target material and the compound containing at least two active methylene function groups can be added to the continuous phase. The target material containing solution can also contain an emulsion stabilizer if desired in the case of a hydrophobic solution. The continuous fluid phase can be vigorously mixed as the target material containing solution is gradually added, thus forming the dispersed core particles within the hydrophilic continuous phase. The mixing can be accomplished by high speed stirring, such as is used in the interfacial polymerization art, or in another conventional manner used in the emulsification art; such as ultrasonically, by shaking, or by employing a colloid mill or homogenizer.

The dispersion conditions, such as the shear rate and degree of agitation, the temperature, and the volumetric ratio of the dispersed base to continuous phase, can be adapted to give the core particle size desired. If high speed stirring is used, the present process permits core particles, and consequently microcapsules having an average diameter of about 0.2 micron and less can be prepared. Conversely, if larger particle sizes are desired, by varying dispersion condition microcapsules having an average diameter of about 100 microns and greater can be prepared.

When the dispersed core particles contain a hydrophobic first reactive compound containing at least two active methylene functional groups, the capsule shells are formed by material which is polymerized from the hydrophobic first reactive compound and a hydrophilic second reactive compound. The hydrophilic second reactive compound in this case is an active methylene reactive crosslinking agent.

In general, the second reactive compound can be added to the continuous phase after the core phase has been dispersed therein. Alternatively, the second reactive compound can be included in the continuous phase before the core phase is dispersed, provided the core phase can be dispersed before substantial reaction between the first and second reactive compounds.

If desired, the target material initially can be dispersed in the continuous phase. The first reactive material can be added to the system with mixing, to permit the first reactive material to mix with the dispersed phase. Subsequently, the second reactive material can be added to the system. The order of addition of the first and second reactive materials can be reversed provided that the time constant for mixing is short compared with the time constant for reactions between the first and second reactive compounds or provided the reaction will be subsequently catalyzed, for example, by raising the pH of the system.

Examples of hydrophilic active methylene-reactive crosslinking agents which can be used include hydrophilic aldehydes, latent aldehydes hydrophilic bis(alkylidenes) of compounds containing at least two active methylene groups, hydrophilic alpha, beta-ethylenically unsaturated carbonyl compounds, and hydrophilic hydrazones.

Examples of hydrophilic aldehydes which can be used include formaldehyde, glyoxal, glutaraldehyde, furfural, acrolein, methacrolein, propionaldehyde, acetaldehyde and crotonaldehyde.

By latent aldehyde is meant a compound which will generate an aldehyde in-situ in the reaction mixture under appropriate reaction conditions. Examples of latent aldehydes include: adducts of a bisulfate salt and an aldehyde (having a functional group having the formula $-C(OH)SO_3^-M^+$, where M is selected from the alkali metals); hemiacetals; acetals; adducts of an aldehyde and ammonia, such as hexamethyltetraamine, hexahydro-2,4,6-trimethyl-1,3,5-triazine, and aminals (compounds having a functional group having the formula $-C(OH)HNH_2$ or $-CH(NR_2)_2$ where R is alkyl); imines; hydrazones and substituted hydrazones (substituted, for example, with aromatic groups such as 2,4-dinitrophenyl); azines; semicarbazones; oximes; enamines; alkyldine bisamides (compounds having a functional group having the structural formula $-CH[N-C(O)R_2]_2$ where $R_2$ is alkyl); alpha-aminoalkenesulfonic acids; cyanohydrins; 1,3-oxazolidines; enol esters including enol acetates; and enol esters. Specific examples of latent aldehydes which generate hydrophilic aldehydes include aldehyde bisulfite addition product, and amino alkene sulfonic acids.

By alkylidene of an active methylene group is meant a functional group having the structural formula $$-X-C(O)-C(Z)=CHR_3$$

where X and Z are given above and $R_3$ is hydrogen or ($C_1$-$C_{18}$) hydrocarboyl including ($C_1$-$C_{18}$)alkyl, ($C_7$-$C_{18}$)aralkyl, ($C_2$-$C_{18}$) alkenyl, ($C_7$-$C_{18}$)alkaryl, ($C_8$-$C_{18}$)alkaralkyl, ($C_8$-$C_{18}$) alkenaryl, ($C_8$-$C_{18}$)aralkenyl, and the like. Specific examples of hydrophilic bisalkylidenes of compounds having at least two active methylene groups per molecule include bis(isopropylidinecyanoacetyl)pentaerythritol, etc.

Examples of hydrophilic alpha, beta-ethylenically unsaturated carbonyl compounds include hydrophilic alpha, beta-ethylenically unsaturated aldehydes such as acrolein and methacrolein. An example of a hydrophilic amine is phenylenediamine The temperature and pH of the continuous fluid phase are preferably adjusted to promote reaction between the first and second reactive compounds. This can be accomplished after the core particles have been dispersed within the continuous phase. For example, in the case of a base-catalyzed reaction, a solution of strong base can be added after the core particles are formed and the first and second reactive compounds have been added to raise the pH of the reaction mixture. The optimum reaction conditions depend on the identity of the first and second reactive compounds.

In general, it is preferred that stoichiometric proportions of the first and second reactive compounds be employed. The amount of first and second reactive compounds can be calculated from the particle size of the microcapsules to be formed, the desired shell thickness, and the amount of target material to be encapsulated. In general, the shell thickness will vary with the application for which the microcapsules are to be employed and the physical properties of the polymer formed by the reaction between the first and second reactive compounds. For example, rigid, impermeable relatively thin shells may be favored for applications in which the microcapsules are to be ruptured by applied pressure, such as in scent delivery and carbonless copy paper applications, whereas relatively thick, relatively permeable low modulus shells may be favored for applications calling for sustained release of the target material.

The reaction between compounds containing at least one active methylene group and an aldehyde is well known in the organic chemical arts, and is known as the Knovenagel condensation reaction. The Knovenagel reaction is reviewed in J. Jones, "The Knovenagel Condensation," *Organic Reactions*, Vol. 15 (A. C. Cope ed., John Wiley & Sons, New York 1967) 204–582 and is summarized in J. March, *Advanced Organic Chemistry* (Third Edition, John Wiley & Sons, New York 1985) 835–841. When the active methylene crosslinking agent is an alpha, beta-ethylenically unsaturated carbonyl compound, the reaction between the first and second reactive compounds is known as the Michael addition reaction.

While it is presently believed that the shells of the microcapsules are formed by a polymerization reaction between the first and second reactive compounds at or near the interface between the continuous and dispersed phases, the process of the present invention is not limited to include specific polymerization sites, and includes embodiments in which polymerization occurs in-situ in either the continuous or dispersed phase, with subsequent diffusion or migration of the polymeric material to the interface between the phases.

If desired the first reactive compound can be chosen to be a compound having at least two active methylene functional groups per molecule and the second reactive compound can be chosen to be an active methylene-reactive crosslinking agent. This embodiment of the present process may be desirable when, for example, the target material itself has some reactivity with respect to the active methylene functional groups. For example, when the target material is a weakly reactive aldehyde, the present embodiment is preferred.

In the case in which the continuous fluid phase is hydrophilic, the second reactive compound can then be a hydrophilic compound having at least two active methylene groups per molecule. For example, the second reactive compound can be the reaction product of an ethoxylated or ethoxylated/proxylated di- or polyol with a compound having the structural formula $$H—X^1—C(O)—CH_2—Z$$

where Z is given above and $X^1$ is X above, excluding $X=—O—(CH_2CH_2O)_m[CH(CH_3)CH_2\ \ O]_n$. The ethoxylation and ethoxylation/propoxylation of alcohols, including diols and polyols, is well known in the preparative chemical arts. See, for example, H. Greenwald et al., *Surfactant Science Series*, Vol. I, Chapter 2, pp. 8-43, Ed. Martin J. Schick, Marcel Dekker, Inc., N.Y., N.Y. Examples of diols and polyols which can be used are given above. Specific examples of hydrophilic compounds having at least two active methylene functional groups include tris[cyanoacetyl- (ethoxy)$_5$]-glycerol, tris[cyanoacetyl(ethoxy)$_6$]trimethylolpropane, tris[nitroacetyl(ethoxy)$_5$]glycerol, di[-cyanoacetyl(ethoxy)$_7$]trimethylolpropane, and tetra[acetoacetyl(ethoxy)$_5$]pentaerythritol.

When the second reactive compound is a hydrophilic compound having at least two active methylene groups per molecule, the first reactive compound is preferred to be a hydrophobic active methylene-reactive crosslinking agent. Examples of hydrophobic active methylene-reactive crosslinking agents include hydrophobic aldehydes, latent aldehydes giving hydrophobic aldehydes, hydrophobic alkylidenes of compounds having at least two active methylene groups per molecule, hydrophobic alpha, beta-ethylenically unsaturated carbonyl compounds, and hydrophobic amines. Specific examples of hydrophobic aldehydes include n-octyl aldehyde, n-nonyl aldehyde, n-decylaldehyde, lauryl aldehyde, n-heptaldehyde, and stearaldehyde. Specific examples of latent aldehydes giving hydrophobic aldehydes include n-octylaldehyde cyanohydrin, the phenylhydrazone of n-nonylaldehyde, and the ethanol acetal of stearaldehyde. Examples of hydrophobic alkylidene compounds having at least two active methylene groups per molecule include tris(isopropylidinecyanoacetyl)trimethylolpropane.

In addition to those previously described embodiments of the present process in which the continuous fluid phase is hydrophilic and the dispersed core phase is hydrophobic, the present invention also includes embodiments in which a hydrophilic core phase is dispersed in a hydrophobic continuous fluid phase, such as water-in-oil emulsions. Thus, the present process can be used to encapsulate hydrophilic target materials. In this embodiment of the process it is preferred that the continuous fluid phase be a hydrophobic fluid which is immiscible with water and that the core phase, including the target material be water-soluble. Examples of water-soluble target materials which can be encapsulated using this embodiment of the process include Kathon ® 886 NW biocide, salts of ethylenebisdithiocarbomate, such as Dithane ® D-14 fungicide, choline chloride, aldehydes such as formaldehyde, inorganic salts such as zinc acetate, and free radical-generating compounds such as ammonium persulfate.

The same techniques as described above for forming a hydrophobic core phase in a hydrophilic continuous fluid phase may in general be used to disperse a hydrophilic core phase in a hydrophobic continuous phase. For example, the hydrophilic core phase can be dispersed by gradually adding an aqueous solution containing a hydrophilic water-soluble target material, and a hydrophilic water-soluble first reactive compound, to a hydrophobic, substantially water-insoluble continuous fluid phase. As in the case of the hydrophobic core phase dispersed in a hydrophilic continuous phase, the hydrophilic first reactive compound which is dispersed or dissolved in the hydrophilic core phase can be either a compound having at least two active methylene functional groups per molecule, or an active methylene-reactive crosslinking agent; it being understood that the hydrophobic second reactive compound will then be either an active methylene-reactive crosslinking agent or a compound having at least two active methylene groups per molecule, respectively.

The hydrophobic continuous fluid phase can comprise an organic solvent, such as xylene, toluene, mineral spirits, or the like, or mixtures thereof.

If desired, conventional water-in-oil dispersants and/or stabilizers can be employed. An example of a polymeric AND (nonaqueous dispersion) dispersing agent is a block copolymer having a polyhydroxystearic acid block and a polyacrylate block, the polyacrylate block being polymerized from monomer including hydroxyethyl acrylate. Similarly, surface active agents can be employed to stabilize the emulsion of hydrophilic core particles in the hydrophobic continuous phase, as is well known in the art. Examples of surface active agents which can be used to stabilize the dispersed hydrophilic core phase in the continuous hydrophobic phase include Span ® (trademark of ICI Americas Inc.) 80 (sorbitan monooleate, HLB =4.3), and Triton ® X-15 (trademark of Rohm and Haas Company) (t-octylphenol ethoxylate, HLB=3.6).

A dispersing agent such as a surface active agent can be used to aid in dispersing the hydrophilic target material within the core particles and to aid in emulsifying and stabilizing the core particles. For example, the core phase can include conventional surface active agents such as the dialkyl sulfosuccinates, for example, diethylhexyl sulfosuccinate, and Triton ® X-400 (stearyldimethylbenzylammonium chloride).

After the polymeric shells have been formed around the core phase particles, the microcapsules can be separated from the continuous phase by any process known in the physical separation arts, such as by filtration, decantation, centrifugation, flash drying, spray drying, freeze drying, evaporation, distillation, and the like. The separation process selected is preferably chosen to effect a rapid and efficient separation, with a minimum of mechanical damage to or disruption of the microcapsules. In some cases, it may be desirable to use the microcapsules dispersed in the continuous phase directly in an application, such as when the microcapsules are to be coated onto sheet stock or other surface. If desired, additional components can be added to or dissolved in the continuous phase prior to use.

In one embodiment of the present process, the microcapsules contain crosslinking reagents for coating composition binders as target materials, and the shells of the microcapsulves are selected to permit gradual release of the cross-linking reagent from the microcapsules after the coating composition has been applied to the surface to be coated. The microcapsules can contain a difunctional crosslinking reagent for the coating composition binder, such as a diisocyanate or a diepoxide, and the capsule shell is formed to permit gradual release of the crosslinking agent to crosslink the binder while the coating composition is drying.

The following examples will aid those skilled in the art in understanding the process of the present invention, however, the present invention is in no way limited thereby. In the following examples precentage composition is by weight.

EXAMPLE 1

Microencapsulation of Hydrophobic Target Material Using a Hydrophilic Crosslinking Agent A continuous aqueous phase was prepared by mixing together 500 g of an aqueous solution of a six percent Vinol ® (trademark of Air Products) 205 polyvinyl alcohol, 625 g water, and 60 g of an aqueous solution of a one percent diethylhexylsulfosuccinate. A hydrophobic solution phase was prepared by mixing 80 g 1-pentanol, 320 g Skane ® M-8 biocide (N-octylisothiazolone), 42 g dioctyl phthalate and 700 g tris(acetoacetyl)-trimethylolpropane. The aqueous solution was added all at once to the hydrophobic solution and the mixture was homogenized using a Ross Homogenizer by stirring at 18,000 rpm for approximately ten minutes. The emulsified mixture was transferred to a 5 liter flask and the emulsification vessel (a half-gallon jar) was rinsed with a mixture of 250 g of six percent Vinol ® 205 aqueous solution and 356 g of water, the rinse fluid being added to the flask. To the emulsified mixture was added gradually while stirring vigorously a mixture of 190 g of a 37% aqueous solution of formaldehyde and 416 g water. Next, a mixture of 7.2 g of 50% sodium hydroxide and 72 g water was added to the reaction mixture. Stirring was continued for about sixty minutes, and the resulting dispersion of microcapsules in the aqueous continuous phase was filtered through cheesecloth.

EXAMPLE 2

Microencapsulation of a Hydrophilic Target Material Using a Hydrophilic Crosslinker A continuous hydrophobic organic phase was prepared by mixing together 174 g xylene, 174 g odorless mineral spirits, 6 g Span ® 80 surfactant (sorbitan monooleate), 48 g of a block copolymer of polyhydroxystearic acid and polyhydroxyethylacrylate (35%) and 72g tris(acetoacetyl)trimethylolpropane. An aqueous phase was prepared by mixing 180g water, 180g Kathon ® 886 MW biocide, and 44.4 g of a seven percent aqueous solution of diethyl sulfosuccinate. The aqueous phase was added all at once to the hydrophobic organic phase and the mixture was homogenized using a Ross Homogenizer by stirring at about 18,000 rpm for approximately five minutes. The homogenizer speed was reduced to about 5,000 rpm and 45 g of a two percent aqueous solution of sodium hydroxide was added to the homogenized mixture. After an additional 2-3 minutes 23.2 g of a seven percent aqueous solution of formaldehyde was added to the homogenized mixture and stirring was continued for several additional minutes in the homogenizer. Next, the homogenized mixture was transferred to a flask and was stirred with a mechanical stirrer for about 15-20 minutes. Finally, the dispersion of microcapsules in the continuous organic phase was filtered through cheesecloth.

During the homogenization step the temperature of the mixture increases, the temperature increase being a function of volume. With moderate volumes (about one liter) temperatures of up to about 45° C. are observed. Before adding base and crosslinker, the mixture is preferably cooled to room temperature using cold water.

EXAMPLE 3

Microencapsulation of a Hydrophobic Target Compound Using a Hydrophobic Crosslinker A continuous aqueous phase was prepared by mixing together 16.7 g of six percent aqueous solution of Vinol ® 205 polyvinylalcohol, 21.7 g water, 3 g of a one percent aqueous solution of diethylsulfosuccinate, and 20.6 g of tris[cyanoacetyl(ethoxy)$_5$]glycerol. A hydrophobic organic phase solution was prepared by mixing together 6 g 1-pentanol, 1.4 g dioctyl phthalate, 5 g toluene, 4.3 g n-octyl aldehyde, and 0.6 g Skane ® M-8 mildicide. The aqueous phase was added to the organic phase and homogenized at about 18,000 rpm using a Ross Homogenizer for approximately 10 minutes. The homogenizer speed was reduced to approximate 1,800 rpm and 2.2 g of a two percent aqueous solution of sodium hydroxide was added. After 2-3 minutes, the homogenized mixture was transferred to a magnetic stir plate and stirring was continued for 20 minutes, and the microcapsule containing dispersion was filtered through cheese-cloth.

EXAMPLE 4

Microencapsulation of a Hydrophilic Target Compound Using a Hydrophobic Crosslinker A continuous hydrophobic organic phase was prepared by mixing together 0.5 g sorbitan monooleate, 14.5 g xylene, 14.5 g odorless mineral spirits, 4.0 g 35% solution of a block copolymer of polyhydroxystearic acid and polyhydroxyethylacrylate, and 2.2 g octyl aldehyde. An aqueous phase was prepared by mixing together 3.7 g of a seven percent solution of diethylsulfosuccinate, 7.5 g water, 15 g of Kathon ® 886 MW biocide, and 10.3 g tris[cyanoacetyl(ethoxy)$_5$] glycerol. The aqueous phase was added to the hydrophobic phase and homogenized at about 18,000 rpm in a Ross Homogenizer for approximately five minutes. The homogenizer speed was reduced to about 5,000 rpm and 1.1 g of a two percent aqueous solution of sodium hydroxide was added. After 2-3 minutes the homogenized mixture was transferred to a magnetic stir plate and stirred for 15-20 minutes. The microcapsule containing dispersion was filtered through cheesecloth.

EXAMPLE 5

Crosslinking A Coating Composition Binder Using Microencapsulated Epoxy

A dispersion of encapsulated Epon ® (trademark of Shell) 830 resin (diepoxide of bisphenol A) is prepared according to Example 1 above. The dispersion is prepared to contain 50 milliequivalents of epoxy per 100 g dispersion. The dispersion is blended with an amine-functional coating binder resin containing 52 milliequivalents amine per 100 g resin. Therefore, 100 g dispersion are to be blended with 96 g resin, and a film is to be cast from the blend. When dried and cured at room temperature, the film will be found to be swellable but insoluble in a solvent for the amine resin, such as acetone. The blend will show a gradual viscosity increase over several weeks, while a control blend of Epon ® 830 resin and the amine-functional resin will gel within a day or so. Said amine functional resin could be utilized in applications such as adhesives, binders, caulks, coatings, mastics, etc.

Using substantially the same processes as given in Examples 1 and 2 above, the following additional examples of microencapsulated target materials were prepared according to the present invention:

| Example | Active Methylene | Cross-linker | Target Material | Cont. Phase |
|---|---|---|---|---|
| 6 | A[1] | HCHO | butyl acetate | Aq (Aqueous) |
| 7 | " | " | S-150[10] | Aq |
| 8 | " | " | Skane ®[14] | Aq |
| 9 | " | " | S-150 | Aq |
| 10 | " | " | Skane ® | Aq |
| 11 | " | " | " | Aq |
| 12 | " | " | water | Or (Organic) |
| 13 | " | " | Kathon ®[11] | Or |
| 14 | " | " | Dithane ®[12] | Or |
| 15 | " | " | Kathon ® | Or |
| 16 | " | " | water | Or |
| 17 | " | " | choline | Or |
| 18 | " | " | Skane ® | Aq |
| 19 | " | " | " | Aq |
| 20 | " | " | Karathane ®[13] | Aq |
| 21 | " | " | Kathon ® | Or |
| 22 | B[2] | " | Skane ® | Aq |
| 23 | C[3] | " | " | Aq |
| 24 | A | " | ammonium persulfate | Or |
| 25 | " | glyoxal | Skane ® | Aq |
| 26 | " | acrolein | " | Aq |
| 27 | " | glutaraldehyde | " | Aq |
| 28 | " | furfural | " | Aq |
| 29 | " | HCHO | Kathon ® | Or |
| 30 | " | " | choline | Or |
| 31 | B | " | Kathon ® | Or |
| 32 | C | " | " | Or |
| 33 | A | acrolein | " | Or |
| 34 | " | glutaraldehyde | " | Or |
| 35 | " | HCHO | ammonium persulfate | Or |
| 36 | " | glyoxal | Kathon ® | Or |
| 37 | " | HCHO | phenolphthalein | Or |
| 38 | " | " | Skane ® | Aq |
| 39 | " | " | HCHO | Or |
| 40 | " | " | zinc acetate | Or |
| 41 | A | acrolein | toluene | Aq |
| 42 | " | methacrolein | " | Aq |
| 43 | " | propionaldehyde | " | Aq |
| 44 | " | phenylenediamine | Skane ® | Aq |
| 45 | " | HCHO | " | Aq |
| 46 | D[4]/A | " | " | Aq |
| 47 | A | glucose | " | Aq |
| 48 | E[5] | HCHO | " | Aq |
| 49 | A | " | Kathon ® | Or |
| 50 | D/A | " | " | Or |
| 51 | A | glucose | " | Or |
| 52 | E | HCHO | " | Or |
| 53 | A | " | Skane ® | Aq |
| 54 | " | " | Desmodur ® W[16] | Aq |
| 55 | " | " | Epon 830[17] | Aq |
| 56 | " | " | toluene | Aq |
| 57 | F[6] | " | " | Aq |
| 58 | F | " | Skane ® | Aq |
| 59 | G[7] | " | toluene | Aq |
| 60 | G | " | Skane ® | Aq |
| 61 | H[8]/A | " | toluene | Aq |
| 62 | H/A | " | Skane ® | Aq |
| 63 | A | " | saline | Or |
| 64 | H/A | " | Kathon ® | Or |
| 65 | H/A | " | saline | Or |
| 66 | F | " | Kathon ® | Or |
| 67 | F | " | saline | Or |
| 68 | G | " | Kathon ® | Or |
| 69 | G | " | saline | Or |
| 70 | A | " | Kathon ® | Or |
| 71 | A | " | Desmodur ® W | Aq |
| 72 | A | " | Goal ®[15] | Aq |
| 73 | F | " | " | Aq |
| 74 | G | " | " | Aq |

-continued

| Example | Active Methylene | Cross-linker | Target Material | Cont. Phase |
|---|---|---|---|---|
| 75 | A | " | Skane ® | Aq |
| 76 | I[9] | " | toluene | Aq |
| 77 | I | " | Skane ® | Aq |
| 78 | I | " | Kathon ® 886 | Or |
| 79 | I | " | saline | Or |

[1] A = tris(acetoacetyl)trimethylolpropane
[2] B = tris(cyanoacetyl)trimethylolpropane
[3] C = tris(nitroacetoacetyl)trimethylolpropane
[4] D = bis(N-methyl-N-hydroxyethylcyanoacetamido)adipate
D/A is 18.2/11.7 by weight, but is 1/1 by acetoacetate equivalent
[5] E = tris(isopropylidinecyanoacetyl)trimethylolpropane
[6] F = tetra(acetoacetyl)pentaerythritol
[7] G = tetra(acetoacetyl)erythritol
[8] H = bis(acetoacetyl)bisphenol A
H/A is 22.9/11.7 by weight, but is 1/1 by acetoacetate equivalent
[9] I = tris(cyanoacetyl)glycerol
[10] S-150 (Solvesso 150) is now called Aromatic 150, Exxon. It is an alkylbenzene solvent, a mixture of $C_9$–$C_{12}$, mostly $C_{10}$, with a 50% distillation point at 193 C.
[11] "Kathon ®" is N-methyl-5-chloroisothiazolone
[12] "Dithane ®" D-14 is disodium ethylene-1,2-bisdithiocarbamate (nabam)
[13] "Karathane ®" is dinitrooctylphenylcrotonates (dinocap)
[14] "Skane ®" is N-octyl isothiazolone
[15] "Goal ®" is oxyfluorfen
[16] "Desmodur ® W" is bis(4,4'-diisocyanocyclohexyl) methane
[17] "Epon ® 830" is a diepoxide of bisphenol Using substantially the same processes as given in Examples 3 and 4 above, the following additional examples of microencapsulated target materials were prepared:

| Example | Active Methylene | Cross-linker | Target Material | Cont. Phase |
|---|---|---|---|---|
| 80 | B | acetone | Skane ® | Aq (Aqueous) |
| 81 | B | " | toluene | Aq |
| 82 | J[1] | octyl aldehyde | Skane ® | Aq |
| 83 | J | " | toluene | Aq |
| 84 | J | " | Kathon ® 886 | Or (Organic) |
| 85 | J | " | saline | Or |

1. J = tris[cyanoacetyl(ethoxy)5]glycerol

Figure 1:
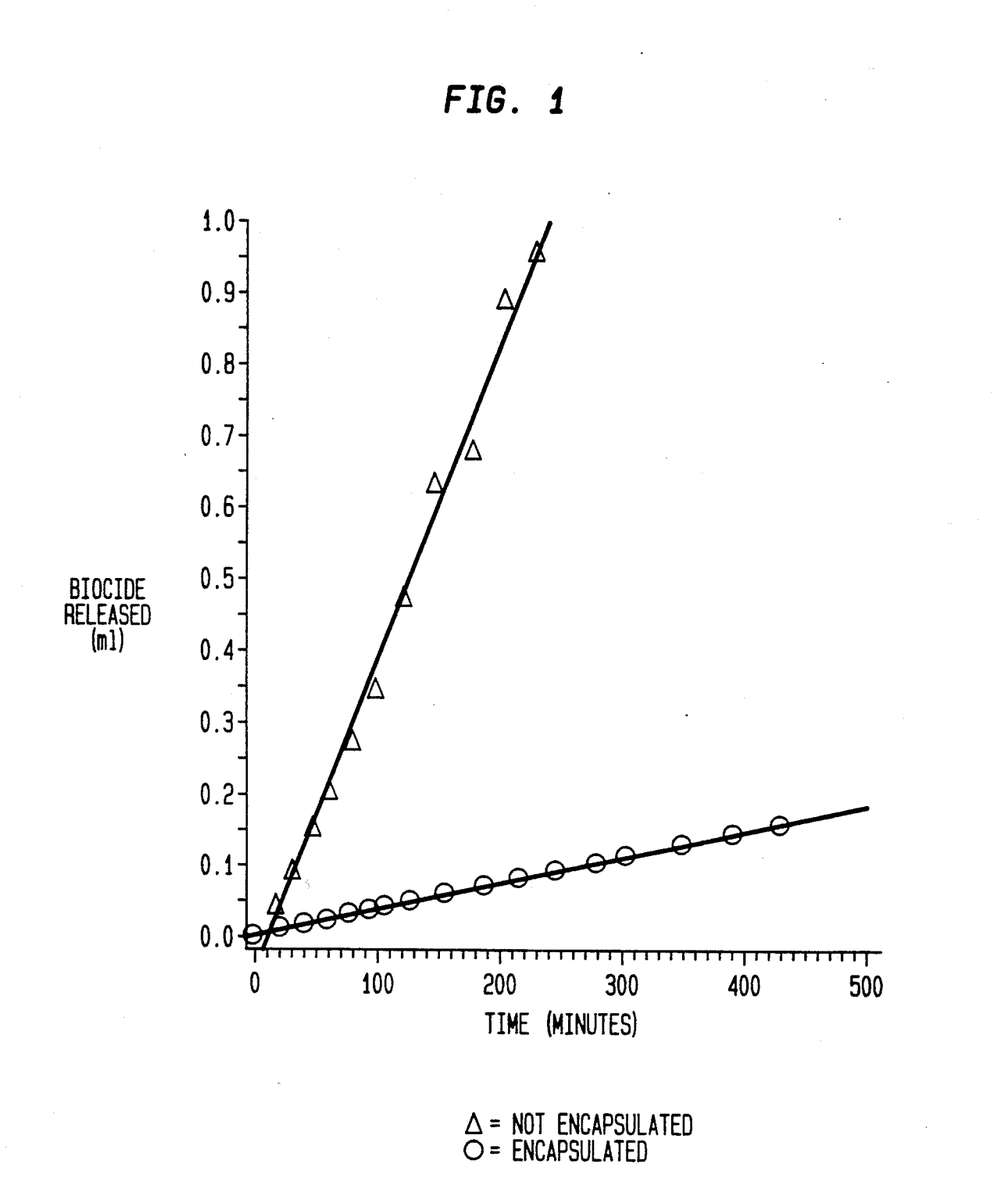
FIG. 1 is a graph illustrating the release of a biocide, Kathon ® 886 NW, from microcapsules prepared according to the present invention.

FIG. 1 illustrates the controlled release of a biocide, Kathon ® 886 MW, from microcapsules prepared according to Example 15. The microcapsules were separated from the continuous phase by air drying. The release of the biocide from the microcapsules was monitored by the following technique.

Usual methods of determining the release rate of target compounds from formulated materials, e.g. drugs or agricultural chemicals, is complicated in the present case because of the colloidal nature of the products of the present process. This requires the separation of the released compound from the unreleased formulated compound. For this reason we have developed a release measuring system in which the compound is released from the formulation and then separated via diffusion through a set of hollow fiber dialysis membranes. Since a part of this system is just the diffusion of the free compound through the hollow fibers, all release measurements are compared to a control of unformulated compound, thus a relative release rate is determined. Further, by comparing all runs to a control, any differences between hollow fiber sets are normalized.

In order to make the measurement, a constant level of target material is dispersed into a set weight of water. A hollow fiber set, in the shape of a U is placed into the dispersion including the target material. Water is pumped through the hollow fibers, at a specific rate, into a reservoir with a preset weight of water. The target material diffuses from inside the microcapsules into the disperse aqueous phase, and then through the hollow fiber membrane into the reservoir system. The accumulation of the target material in the reservoir system is monitored by sampling the reservoir at various times throughout the run. FIG. 1 illustrates the relative, normalized results obtained for release of Kathon ® 886 MW from microcapsules prepared according to Example 15. The target material was transferred at a rate of 4.6 mg/ml/min. while unencapsulated material was transferred to the reservoir at a rate of 52.2 mg/ml/min.

Figure 2:
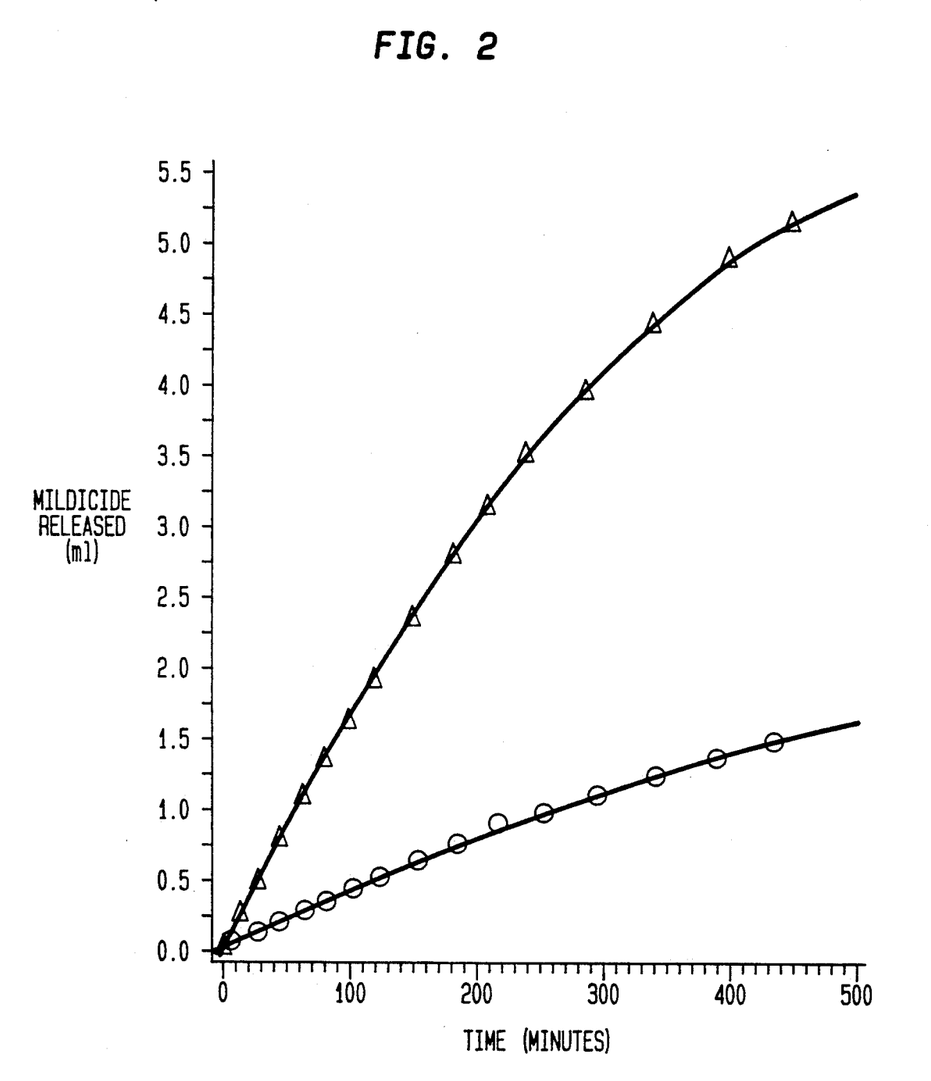
FIG. 2 is a graph illustrating the release of a mildicide, Skane ® M-8, from microcapsules prepared according to the present invention.

FIG. 2 illustrates the controlled release of a mildicide, Skane ® M-8, from microcapsules prepared according to Example 11. In this case encapsulated target material was transferred to the reservoir at a rate of 170.0 mg/ml/min. while unencapsulated material was transferred at a rate of 716.1 mg/ml/min.

These figures clearly illustrate the controlled release of target materials encapsulated by the present process.

Various modifications can be made in the details of the various embodiments of the process of the present invention, all within the spirit and scope of the invention as defined in the appended claims.

I claim:

1. A coating composition including core-shell particles containing encapsulated target material within walls of condensation polymer product prepared according to the process comprising:
   (a) preparing a core emulsion including a core phase of unpolymerized discrete core particles dispersed in said continuous fluid phase by emulsifying in said continuous fluid phase a mixture comprising:
      (1) a target material, (2) a dispersant for said core particles in said continuous fluid phase;
(b) combining with said target material an unpolymerized first reactive compound insoluble in said continuous fluid phase, said first reactive compound being one of the compounds selected from the group consisting of
  (1) compounds having at least two active methylene functional groups per molecule, and;
  (20 active methylene-reactive crosslinking agents;
(c) combining with said continuous fluid phase an unpolymerized second reactive compound which is soluble or dispersible in said continuous fluid phase and is one of the compounds selected from the group consisting of
  (1) compounds having at least two active methylene functional groups per molecule, and;
  (2) active methylene-reactive crosslinking agents; wherein said second reactive compound is reactive with said first reactive compound; and
(d) reacting said first reactive compound with said second reactive compound to form polymeric encapsulating shells around said core particles, said core-shell particles having a diameter on the order of 0.5 micron and less.

2. An adhesive including core-shell particles containing encapsulated target material within walls of condensation polymer product prepared according to the process comprising:
(a) preparing a core emulsion including a core phase of unpolymerized discrete core particles dispersed in said continuous fluid phase by emulsifying in said continuous fluid phase a mixture comprising:
  (1) a target material,
  (2) a dispersant for said core particles in said continuous fluid phase;
(b) combining with said target material an unpolymerized first reactive compound insoluble in said continuous fluid phase, said first reactive compound being one of the compounds selected from the group consisting of
  (1) compounds having at least two active methylene functional groups per molecule, and;
  (2) active methylene-reactive crosslinking agents;
(c) combining with said continuous fluid phase an unpolymerized second reactive compound which is soluble or dispersible in said continuous fluid phase and is one of the compounds selected from the group consisting of
  (1) compounds having at least two active methylene functional groups per molecule, and;
  (2) active methylene-reactive crosslinking agents; wherein said second reactive compound is reactive with said first reactive compound; and
(d) reacting said first reactive compound with said second reactive compound to form polymeric encapsulating shells around said core particles, said core-shell particles having a diameter on the order of 0.5 micron and less.

3. A mastic composition including core-shell particles containing encapsulated target material within walls of condensation polymer product prepared according to the process comprising:
(a) preparing a core emulsion including a core phase of unpolymerized discrete core particles dispersed in said continuous fluid phase by emulsifying in said continuous fluid phase a mixture comprising;
  (1) a target material,
  (2) a dispersant for said core particles in said continuous fluid phase;
(b) combining with said target material an unpolymerized first reactive compound insoluble in said continuous fluid phase, said first reactive compound being one of the compounds selected from the group consisting of
  (1) compounds having at least two active methylene functional groups per molecule, and;
  (2) active methylene-reactive crosslinking agents;
(c) combining with said continuous fluid phase an unpolymerized second reactive compound which is soluble or dispersible in said continuous fluid phase and is one of the compounds selected from the group consisting of
  (1) compounds having at least two active methylene functional groups per molecule, and;
  (2) active methylene-reactive crosslinking agents; wherein said second reactive compound is reactive with said first reactive compound; and
(d) reacting said first reactive compound with said second reactive compound to form polymeric encapsulating shells around said core particles, said core-shell particles having a diameter on the order of 0.5 micron and less.

4. A caulk including core-shell particles containing encapsulated target material within walls of condensation polymer product prepared according to the process comprising:
(a) preparing a core emulsion including a core phase of unpolymerized discrete core particles dispersed in said continuous fluid phase by emulsifying in said continuous fluid phase a mixture comprising;
  (1) a target material,
  (2) a dispersant for said core particles in said continuous fluid phase;
(b) combining with said target material an unpolymerized first reactive compound insoluble in said continuous fluid phase, said first reactive compound being one of the compounds selected from the group consisting of
  (1) compounds having at least two active methylene functional groups per molecule, and;
  (2) active methylene-reactive crosslinking agents;
(c) combining with said continuous fluid phase an unpolymerized second reactive compound which is soluble or dispersible in said continuous fluid phase and is one of the compounds selected from the group consisting of
  (1) compounds having at least two active methylene functional groups per molecule, and;
  (2) active methylene-reactive crosslinking agents; wherein said second reactive compound is reactive with said first reactive compound; and
(d) reacting said first reactive compound with said second reactive compound to form polymeric encapsulating shells around said core particles, said core-shell particles having a diameter on the order of 0.5 micron and less.

5. A binder composition including core-shell particles containing encapsulated target material within walls of condensation polymer product prepared according to the process comprising:
(a) preparing a core emulsion including a core phase of unpolymerized discrete core particles dispersed in said continuous fluid phase by emulsifying in said continuous fluid phase a mixture comprising;
  (1) a target material, (2) a dispersant for said core particles in said continuous fluid phase;

(b) combining with said target material an unpolymerized first reactive compound insoluble in said continuous fluid phase, said first reactive compound being one of the compounds selected from the group consisting of
   (1) compounds having at least two active methylene functional groups per molecule, and;
   (2) active methylene-reactive crosslinking agents;

(c) combining with said continuous fluid phase an unpolymerized second reactive compound which is soluble or dispersible in said continuous fluid phase and is one of the compounds selected from the group consisting of
   (1) compounds having at least two active methylene functional groups per molecule, and;
   (2) active methylene-reactive crosslinking agents; wherein said second reactive compound is reactive with said first reactive compound; and (d) reacting said first reactive compound with said second reactive compound to form polymeric encapsulating shells around said core particles, said core-shell particles having a diameter on the order of 0.5 micron and less.

6. A coating composition according to claim 1 wherein the coating composition includes a reactive crosslinkable resin and the target material is selected from crosslinking agents for the reactive crosslinkable resin.

7. An adhesive according to claim 2 wherein the adhesive includes a reactive crosslinkable resin and the target material is selected from crosslinking agents for the reactive crosslinkable resin.

8. A mastic according to claim 3 wherein the mastic includes a reactive crosslinkable resin and the target material is selected from crosslinking agents for the reactive crosslinkable resin.

9. A caulk according to claim 4 wherein the caulk includes a reactive crosslinkable resin and the target material is selected from crosslinking agents for the reactive crosslinkable resin.

10. A binder composition according to claim 5 wherein the binder includes a reactive crosslinkable resin and the target material is selected from crosslinking agents for the reactive crosslinkable resin.

* * * * *